US012747217B2

(12) United States Patent
Kaldre et al.

(10) Patent No.: US 12,747,217 B2
(45) Date of Patent: Sep. 29, 2026

(54) PROCESS FOR THE MANUFACTURE OF TETRAZOLE DERIVATIVES

(71) Applicant: Hoffmann-La Roche Inc., Little Falls, NJ (US)

(72) Inventors: Dainis Kaldre, Lörrach (DE); Christian Oliver Kappe, Graz (AT); Christian Steffen Moessner, Lörrach (DE); Peter Sagmeister, Graz (AT); Joerg Mathias Sedelmeier, Basel (CH); Jason Douglas Williams, Graz (AT)

(73) Assignee: Hoffmann-La Roche Inc., Little Falls, NJ (US)

( * ) Notice: Subject to any disclaimer, the term of this patent is extended or adjusted under 35 U.S.C. 154(b) by 479 days.

(21) Appl. No.: 18/321,325

(22) Filed: May 22, 2023

(65) Prior Publication Data

US 2024/0002355 A1 Jan. 4, 2024

Related U.S. Application Data

(63) Continuation of application No. PCT/EP2021/082395, filed on Nov. 22, 2021.

(30) Foreign Application Priority Data

Nov. 23, 2020 (EP) .................................... 20209174

(51) Int. Cl.
*C07D 257/04* (2006.01)
*C07D 487/04* (2006.01)

(52) U.S. Cl.
CPC ......... *C07D 257/04* (2013.01); *C07D 487/04* (2013.01)

(58) Field of Classification Search
CPC ............................ C07D 257/04; C07D 487/04
See application file for complete search history.

(56) References Cited

U.S. PATENT DOCUMENTS

2013/0116236 A1* 5/2013 Adam .................. C07D 487/04 544/254

FOREIGN PATENT DOCUMENTS

JP 2014-532739 12/2014
WO 2007/037468 4/2007

OTHER PUBLICATIONS

Chandgude, A. L. et al. Convergent Three-Component Tetrazole Synthesis. Eur. J. Org. Chem. 2016, 2383-2387. (Year: 2016).*

Roberto, M. F. Translation of a Chemical Reaction from Batch to Continuous Flow via Process Analytical Technology and Chemometrics. Ph.D. Dissertation, University of Washington, 2014. (Year: 2014).*

Glasnov, T. N. et al. The Microwave-to-Flow Paradigm: Translating High-Temperature Batch Microwave Chemistry to Scalable Continuous-Flow Processes. Chem. Eur. J. 2011, 17, 11956-11968. (Year: 2011).*

Chandgude, A. L., et al., "Convergent Three-Component Tetrazole Synthesis" Eur. J. Chem.:2383-2387 (2016).

International Preliminary Report on Patentability—PCT/EP2021/082395 issued May 16, 20023, pp. 1-7.

International Search Report with Written Opinion—PCT/EP2021/082395 mailed Feb. 11, 2022, pp. 1-13.

Li, Lian_Hua, et al., "Transition-metal-free multinitrogenation of amides by C—C bond cleavage: a new approach to tetrazoles" Chem. Commun. 54:11148-11151 ( 2018).

Nettekoven et al., "Novel Triazolopyrimidine-Derived Cannabinoid Receptor 2 Agonists as Potential Treatment for Inflammatory Kidney Diseases" ChemMedChem 11(2):179-189 ( 2016).

* cited by examiner

*Primary Examiner* — Jeffrey H Murray
*Assistant Examiner* — Kristen W Romero
(74) *Attorney, Agent, or Firm* — Robert C. Hall

(57) ABSTRACT

The present invention relates to a process for preparing a compound of formula (I), (I)

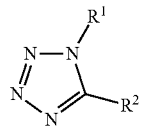

comprising reacting a compound of formula (II)

(II)

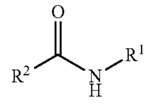

with trimethylsilyl azide ($TMSN_3$) and a chlorinating agent in acetonitrile, wherein the process is performed under continuous-flow conditions and wherein $R^1$ and $R^2$ are as defined in the description.

19 Claims, 1 Drawing Sheet

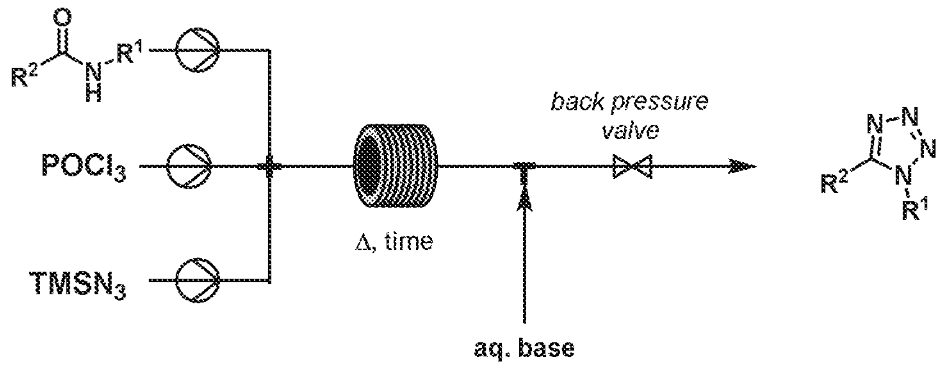
POCl3
TMSN3
Δ, time
back pressure valve
aq. base

PROCESS FOR THE MANUFACTURE OF TETRAZOLE DERIVATIVES

CROSS-REFERENCE TO RELATED APPLICATIONS

This application is a continuation of International Application No. PCT/EP2021/082395 filed on Nov. 22, 2021, which claims priority to European Application No. EP 20209174.0 filed on Nov. 23, 2020, the disclosures of which are incorporated herein by reference.

FIELD OF THE INVENTION

The invention relates in particular to a new process for the manufacture of tetrazole derivatives.

BACKGROUND OF THE INVENTION

Tetrazoles are a class of heterocycles with a wide range of applications in medicinal chemistry and in material sciences and versatile methods to synthesize tetrazoles through safe protocols is highly desirable. Typical procedures use either toxic metals, expensive reagents, harsh reaction conditions and may lead to the formation of dangerous and highly toxic hydrazoic acid ($HN_3$) or explosive sublimates. As such, procedures involving azides including $NaN_3$, $TMSN_3$, $Al(R)_2N_3$, $Sn(R)_2N_3$ or free $HN_3$ have not found broad practical application in organic synthesis, due to the associated safety concerns.

SUMMARY OF THE INVENTION

The applicant has surprisingly found that these problems can be solved and tetrazole derivatives be prepared using a flow chemistry, three components reaction as described below.

The invention thus relates in particular to a process for the preparation of a compound of formula (I)

(I)

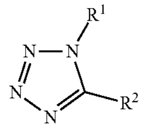

wherein $R^1$ is alkyl, cycloalkyl, aryl, arylalkyl, alkyloxy, alkenyl, alkynyl, heterocyclyl or heteroaryl, all optionally substituted with one to three substituents independently selected from halogen, hydroxyl, alkyl, haloalkyl, hydroxyalkyl, cycloalkyl, halocycloalkyl, hydroxycycloalkyl, alkoxy and cyano;

$R^2$ is —$CH_2$—X or aryl optionally substituted with one to three substituents independently selected from halogen, hydroxyl, alkyl, haloalkyl, hydroxyalkyl, cycloalkyl, halocycloalkyl, hydroxycycloalkyl, alkoxy and cyano;

or $R^1$ and $R^2$ together form alkylene; and

X is halogen, aryloxy, alkyoxycarbonyl, haloalkyl, hydroxyl, mesyl, tosyl, alkoxy, alkylamino or dialkylamino, wherein aryloxy is optionally substituted with one to three substituents independently selected from halogen, hydroxyl, alkyl, haloalkyl, hydroxyalkyl, cycloalkyl, halocycloalkyl, hydroxycycloalkyl, alkoxy and cyano;

comprising the flow chemistry, three components reaction of a compound of formula (II)

(II)

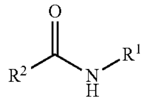

wherein $R^1$ and $R^2$ are as defined above;

with trimethylsilyl azide ($TMSN_3$) and a chlorinating agent in acetonitrile.

The continuous process of the invention can for example be done in microreactors. It offers many benefits such as enhanced heat- and mass transfer characteristics, operation at lower reactor volumes, operation at high temperature/pressure and tighter control of process parameters. The continuous process of the invention can in particular be use in large reactors for large scale production.

In the process of the invention, synthetic intermediates can be generated and consumed in situ (make & consume approach), which eliminates the need to store toxic, reactive, or explosive intermediates and thus makes the synthetic protocol safer. A particularly attractive feature of the present process is the ability to operate without having a head-space where $HN_3$ (bp=37° C.) may accumulate and/or condense. Consequently, the continuous process of the invention mitigates process safety risk associated to azide chemistry.

It was found in particular that acetonitrile is the ideal solvent for the reaction of the invention in regards of kinetics and solubility of starting material, intermediates and product.

$POCl_3$ was found to be the best chlorinating agent in terms of kinetics, solubility and general reaction performance.

Attempts to use an alternative azide source in a biphasic liquid/liquid system failed and the organic soluble $TMSN_3$ was selected for the reaction of the invention.

DESCRIPTION OF THE DRAWINGS

FIG. 1 represents an exemplary reactor setup suitable for running the process of the invention.

DETAILED DESCRIPTION OF THE INVENTION

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl, isopropyl, butyl, isobutyl, tert.-butyl and pentyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular cycloalkyl is cyclopropyl.

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. Particular examples of "alkoxy" are methoxy and ethoxy.

The term "alkylene", alone or in combination, signifies a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene, in particular pentylene.

The term "oxy", alone or in combination, signifies the —O— group.

The terms "halogen" or "halo", alone or in combination, signifies fluorine, chlorine, bromine or iodine and particularly fluorine, chlorine or bromine, more particularly chlorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Particular "haloalkyl" are chloropropyl, fluoromethyl, fluoroethyl, fluoropropyl and fluorobutyl, in particular chloropropyl.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—$NH_2$), the secondary amino group (—NH—) or the tertiary amino group (—N—).

The term "aminocarbonyl, alone or in combination, signifies the —C(O)—$NH_2$ group.

The term "alkenyl", alone or in combination, signifies a monovalent linear or branched hydrocarbon group of 2 to 7 carbon atoms, in particular 2 to 4 carbon atoms, with at least one double bond. Examples of alkenyl include ethenyl, propenyl, prop-2-enyl, isopropenyl, n-butenyl, i-butenyl and t-butenyl.

The term "alkynyl", alone or in combination, signifies a monovalent linear or branched hydrocarbon group of 2 to 7 carbon atoms, in particular from 2 to 4 carbon atoms, and comprising one, two or three triple bonds. Examples of alkynyl include ethynyl, propynyl, prop-2-ynyl, isopropynyl, n-butynyl and iso-butynyl.

The term "aryl", alone or in combination, signifies a monovalent aromatic carbocyclic mono- or bicyclic ring system comprising 6 to 10 carbon ring atoms. Examples of aryl moieties include phenyl and naphthyl, in particular phenyl.

The term "heterocyclyl", alone or in combination, signifies a monovalent saturated or partly unsaturated mono- or bicyclic ring system of 4 to 9 ring atoms, comprising 1, 2, or 3 ring heteroatoms independently selected from N, O and S, the remaining ring atoms being carbon. Examples of monocyclic saturated heterocyclyl are azetidinyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl or dihydropyranyl.

The term "heteroaryl", alone or in combination, signifies a monovalent aromatic heterocyclic mono- or bicyclic ring system of 5 to 12 ring atoms, comprising 1, 2, 3 or 4 heteroatoms independently selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl and acridinyl.

The process according to the invention can be done in a one-pot procedure wherein the three reagents ($POCl_3$, $TMSN_3$, amide of formula (II)) are mixed in a cross at ambient temperature. The reaction mixture can be directed to a tubular reactor where the mixture can be heated for a specific period of time until the conversion of the amide to the desired tetrazole is completed.

To avoid boiling or degassing, the flow system can be operated under pressure. The pressure can be for example between around 1 bar and around 15 bar. The exiting stream can be cooled to ambient temperature and quenched in-line with aqueous base to trap remaining azides. In some preferred embodiments, high pressures are used in combination with high temperatures both as described herein.

Short residence time leads to minimal small volumes of dangerous reaction mixture at any given point, thereby mitigating the risk of explosion compared to larger batch tank reactors.

The invention thus relates in particular to:

A process according to the invention wherein the compound of formula (II) is injected in the flow chemistry reactor at a concentration between around 0.5 M and around 9M, in particular at around 6 M;

A process according to the invention wherein the chlorinating agent is injected in the flow chemistry reactor at a concentration between around 1 M and neat, in particular around 6 M;

A process according to the invention wherein $TMSN_3$ is injected in the flow chemistry reactor at a concentration between around 1M and neat, in particular neat;

A process according to the invention wherein between around 0.9 equivalent and around 2.0 equivalent of $TMSN_3$, in particular around 1.5 equivalent of $TMSN_3$, is present at the start of the three component reaction;

A process according to the invention wherein the compound of formula (II), the chlorinating agent and/or $TMSN_3$ are introduced in the flow chemistry reactor as acetonitrile solutions;

A process according the invention wherein the reaction is performed at a temperature between around 40° C. and around 160° C., in particular between around 60° C. and around 150° C., in particular between around 100° C. and around 140° C.;

A process according the invention wherein the residence time of the reactant in the reaction chamber wherein the flow chemistry, three component reaction takes place is between around 1 minute and around 60 minutes, in particular between around 5 minutes and around 15 or 20 minutes;

A process according to the invention wherein the reaction chamber wherein the flow chemistry, three component reaction takes place doesn't have a headspace;

A process according to the invention wherein the reaction is quenched downstream to the reaction chamber;

A process according to the invention wherein the reaction flow is cooled to a temperature of between around 0 and around 30° C., in particular between around 10 and around 25° C. before the reaction is quenched;

A process according to the invention wherein the reaction is quenched with a base, in particular sodium hydroxide;

A process according to the invention wherein the reaction completion is continuously monitored through NMR, HPLC, IR, MS, UPLC, LC-MS, GC, UV-visible and/or fluorescence spectroscopy;

A process according to the invention wherein $R^1$ is, alkyl, cycloalkyl or arylalkyl;

A process according to the invention wherein $R^1$ is methyl, ethyl, isopropyl, tert.-butyl, cyclopropyl, phenyl or phenylmethyl;

A process according to the invention wherein $R^1$ is alkyl, in particular methyl;

A process according to the invention wherein $R^2$ is $—CH_2—X$;

A process according to the invention wherein X is halogen, aryloxy, alkoxycarbonyl or haloalkyl;

A process according to the invention wherein X is chlorine, bromine, iodine, phenyloxy, ethyloxycarbonyl or chloropropyl;

A process according to the invention wherein X is halogen, in particular chlorine, bromine or iodine, more particularly chloride;

A process according to the invention wherein the chlorinating agent is $POCl_3$, $SOCl_2$, $SO_2Cl_2$ or cyanuric chloride, in particular $POCl_3$;

A process according to the invention wherein the compound of formula (I) is selected from 5-(chloromethyl)-1-methyl-tetrazole; 5-(bromomethyl)-1-methyl-tetrazole; 5-(iodomethyl)-1-methyl-tetrazole; 1-methyl-5-(phenoxymethyl)tetrazole; ethyl 2-(1-methyltetrazol-5-yl)acetate; 1-methyl-5-phenyl-tetrazole; 5-(4-fluorophenyl)-1-methyl-tetrazole; 5-(4-methoxyphenyl)-1-methyl-tetrazole; 5-(chloromethyl)-1-propyl-tetrazole; 5-(chloromethyl)-1-isopropyl-tetrazole; 5-(chloromethyl)-1-cyclopropyl-tetrazole; 1-tert-butyl-5-(chloromethyl)tetrazole; 1-benzyl-5-(chloromethyl)tetrazole; 5-(chloromethyl)-1-phenyl-tetrazole; 6,7,8,9-tetrahydro-5H-tetrazolo[1,5-a]azepine; and 5-(4-chlorobutyl)-1-cyclohexyl-tetrazole; or a salt thereof.

A process according to the invention wherein the compound of formula (I) is 5-(chloromethyl)-1-methyl-1H-tetrazole;

A process according to the invention wherein the compound of formula (II) is 2-chloro-N-methyl-acetamide;

A process according to the invention wherein the compound of formula (I) is 5-(chloromethyl)-1-methyl-1H-tetrazole, the compound of formula (II) is 2-chloro-N-methyl-acetamide and the chlorinating agent is $POCl_3$.

A process for the manufacture of 5-(chloromethyl)-1-methyl-1H-tetrazole comprising the flow chemistry, three component reaction of 2-chloro-N-methyl-acetamide with $POCl_3$ and trimethylsilyl azide in acetonitrile; and A process according to the invention further comprising the reaction of 5-(chloromethyl)-1-methyl-1H-tetrazole with trifluoro-acetic acid (S)-1-(5-tert-butyl-3H-[1,2,3]triazolo[4,5-d]pyrimidin-7-yl)-pyrrolidin-3-yl-ester in the presence of a base to arrive at (S)-1-[5-tert-butyl-3-(1-methyl-1H-tetrazol-5-ylmethyl)-3H-[1,2,3]triazolo[4,5-d]pyrimidin-7-yl]-pyrrolidin-3-ol.

The invention further comprises the preparation of compound of formula (IV), (IV)

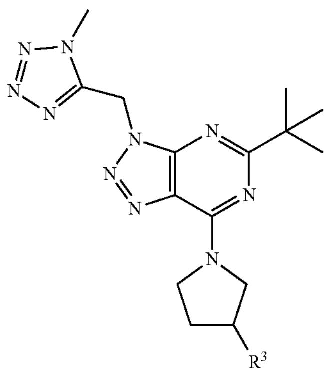

wherein $R^3$ is halogen, aryloxy, alkyoxycarbonyl, haloalkyl, hydroxyl, mesyl, tosyl, alkoxy, alkylamino or dialkylamino, wherein aryloxy is optionally substituted with one to three substituents independently selected from halogen, hydroxyl, alkyl, haloalkyl, hydroxyalkyl, cycloalkyl, halocycloalkyl, hydroxycycloalkyl, alkoxy and cyano, particularly hydroxyl, mesyl, and tosyl, more particularly hydroxyl;

comprising the reaction of compound of formula (I), (I)

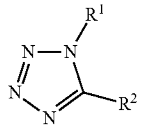

wherein $R^1$ is alkyl, cycloalkyl, aryl, arylalkyl, alkyloxy, alkenyl, alkynyl, heterocyclyl or heteroaryl, all optionally substituted with one to three substituents independently selected from halogen, hydroxyl, alkyl, haloalkyl, hydroxyalkyl, cycloalkyl, halocycloalkyl, hydroxycycloalkyl, alkoxy and cyano;

$R^2$ is $—CH_2—X$ or aryl optionally substituted with one to three substituents independently selected from halogen, hydroxyl, alkyl, haloalkyl, hydroxyalkyl, cycloalkyl, halocycloalkyl, hydroxycycloalkyl, alkoxy and cyano;

or $R^1$ and $R^2$ together form alkylene; and

X is halogen, aryloxy, alkyoxycarbonyl, haloalkyl, hydroxyl, mesyl, tosyl, alkoxy, alkylamino or dialkylamino, wherein aryloxy is optionally substituted with one to three substituents independently selected from halogen, hydroxyl, alkyl, haloalkyl, hydroxyalkyl, cycloalkyl, halocycloalkyl, hydroxycycloalkyl, alkoxy and cyano;

with the compound of formula (III), (III)

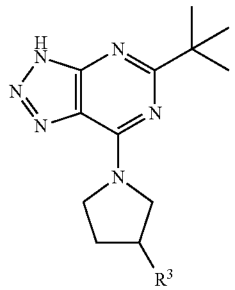

wherein $R^3$ is as described above.

Compound (IV) could be purified following standard laboratory methods (e.g. crystallization, HPLC, column chromatography, distillation).

The class of compounds disclosed in WO2013/068306 have shown activities as CB2 receptor agonist. The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

The invention will now be illustrated by the following examples which have no limiting character.

EXAMPLES

Example 1

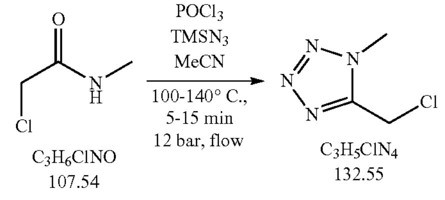

The reaction was done according to the reactor setup represented in FIG. 1.

Feed solutions of 2-Chloro-N-methylacetamide (6.0 M in acetonitrile), $POCl_3$ (10.59 M, neat) and TMS-azide (7.35M neat) are prepared and the individual flow rates are controlled to meet 1.00 equivalent of 2-Chloro-N-methylacetamide, 1.03 equivalent of $POCl_3$ and 1.5 equivalent of TMS-azide in the reactor. The initiation of the setup occurs in a continuous fashion with pumps and transfer lines being purged with the individual reagent stream. The reactor content is adjusted to about 112.5° C. and about 8-12 bar system pressure with residence time of about 12.5 min. The exiting reaction mass is then cooled to room temperature and quenched in a mixer with aqueous 6M NaOH solution and isopropyl acetate (iPrOAc) or diethylcarbonate and pH is constantly kept 9-10 with feedback loop. Phases are separated either batch-wise or continuously using a mixer settler unit and the aqueous phase is extracted with iPrOAc in a second mixer/settler unit. The combined organic phase is collected in a batch mode for further batch isolation. Distillation of the organic layer, anti-solvent addition, washing of the filter cake and drying affords the product in about 70-80% yield as a beige solid.

Preferably, all hardware components used are made of plastics (non-limiting examples are peek, PTFE, and PFA), glass, or glass-lined to ensure material compatibility and process safety.

Example 2

Following the procedure described in Example 1, the following reactions have been carried out.

| Entry | Starting material | Product | Yield |
|---|---|---|---|
| 1 | 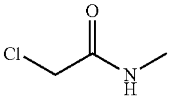 | 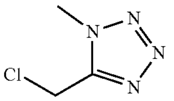 | 84% |
| 2 | 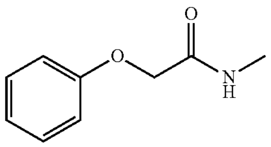 | 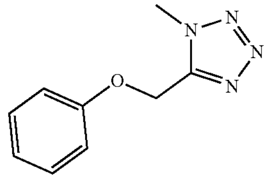 | 99% |
| 3 | 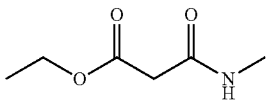 | 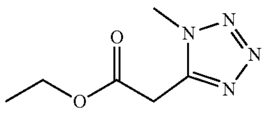 | 81% |

-continued
| Entry | Starting material | Product | Yield |
|---|---|---|---|
| 4 | 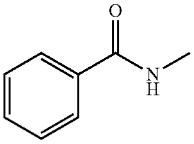 | 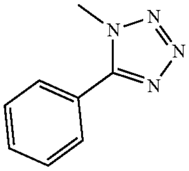 | 55% |
| 5 | 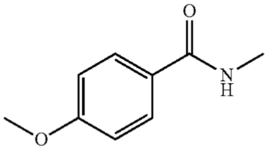 | 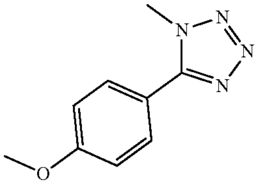 | 24% |
| 6 | 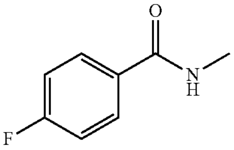 | 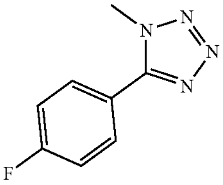 | 51% |
| 7 | 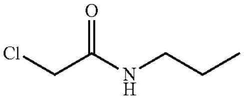 | 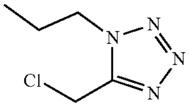 | 84% |
| 8 | 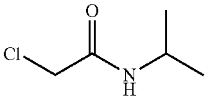 | 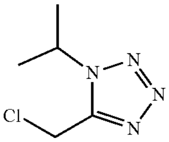 | 84% |
| 9 | 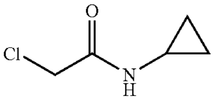 | 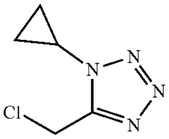 | 86% |
| 10 | 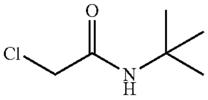 | 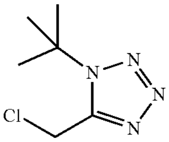 | 11% |
| 11 | 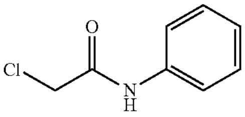 [SMILES: O=C(CCl)Nc1ccccc1] | 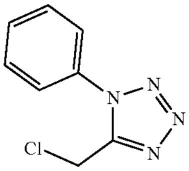 [SMILES: ClCc1nnnn1-c1ccccc1] | 4% |
| 12 | 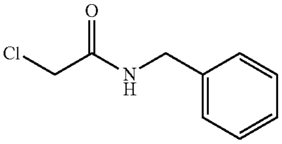 [SMILES: O=C(CCl)NCc1ccccc1] | 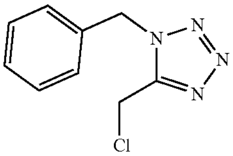 [SMILES: ClCc1nnnn1Cc1ccccc1] | 71% |

-continued

| Entry | Starting material | Product | Yield |
|---|---|---|---|
| 13 | 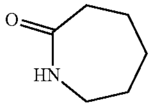 | 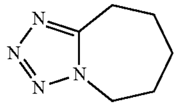 | 74% |
| 14 | 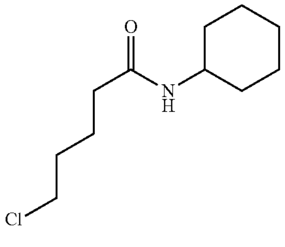 [SMILES: O=C(CCCCCl)NC1CCCCC1] | 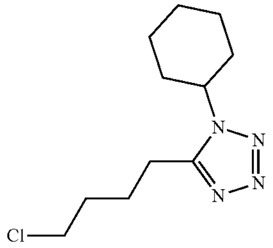 [SMILES: ClCCCCc1nnnn1C1CCCCC1] | 86% |

The invention claimed is:

1. A process for the preparation of a compound of formula (I)

(I)

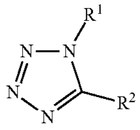

wherein $R^1$ is alkyl, cycloalkyl, aryl, or arylalkyl;

$R^2$ is: —$CH_2$—X; or aryl optionally substituted with one substituent independently selected from halogen, and alkoxy;

or $R^1$ and $R^2$ together form alkylene; and

X is halogen, aryloxy, alkyoxycarbonyl, or haloalkyl;

comprising reacting a compound of formula (II)

(II)

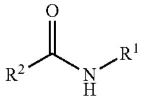

wherein $R^1$ and $R^2$ are as defined above;

with trimethylsilyl azide ($TMSN_3$) and $POCl_3$ in acetonitrile under continuous-flow conditions.

2. The process according to claim 1, wherein the compound of formula (II) is injected in the flow chemistry reactor at a concentration of 6 M.

3. The process according to claim 1, wherein $POCl_3$ is injected in the flow chemistry reactor at a concentration of 6 M.

4. The process according to claim 1, wherein $TMSN_3$ is injected in the flow chemistry reactor neat.

5. The process according to claim 1, wherein 1.5 equivalent of $TMSN_3$, is present at the start of the three component reaction.

6. The process according to claim 1, wherein the compound of formula (II), $POCl_3$ and/or $TMSN_3$ are introduced in the flow chemistry reactor as acetonitrile solutions.

7. The process according to claim 1, wherein the reaction is performed at a temperature of 112.5° C.

8. The process according to claim 1, wherein the residence time of the reactant in the reaction chamber wherein the flow chemistry, three component reaction takes place is 12.5 minutes.

9. The process according to claim 1, wherein the reaction flow is cooled to room temperature before the reaction is quenched.

10. The process according to claim 1, wherein the reaction is quenched with sodium hydroxide.

11. The process according to claim 1, wherein the reaction is monitored through NMR, HPLC, IR, MS, UPLC, LC-MS, GC, UV-visible and/or fluorescence spectroscopy.

12. The process according to claim 1, wherein $R^1$ is, alkyl, cycloalkyl or arylalkyl.

13. The process according to claim 1, wherein $R^1$ is alkyl.

14. The process according to claim 1, wherein $R^2$ is —$CH_2$—X.

15. The process according to claim 1, wherein X is halogen.

16. The process according to claim 1, wherein X is chlorine, bromine or iodine.

17. The process according to claim 1, wherein the compound of formula (I) is 5-(chloromethyl)-1-methyl-1H-tetrazole, and the compound of formula (II) is 2-chloro-N-methyl-acetamide.

18. The process according to claim 1, wherein $R^1$ is methyl and $R^2$ is chloromethyl such that the compound of formula (1) is 5-(chloromethyl)-1-methyl-1H-tetrazole

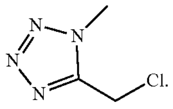

19. The process according to claim 18, further comprising:

reacting 5-(chloromethyl)-1-methyl-1H-tetrazole

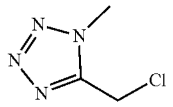

with trifluoro-acetic acid (S)-1-(5-tert-butyl-3H-[1,2,3]triazolo[4,5-d]pyrimidin-7-yl)-pyrrolidin-3-yl-ester
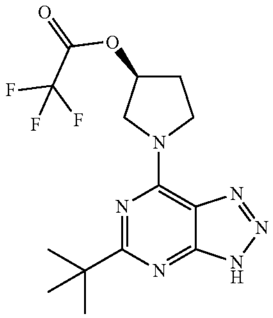 [SMILES: CC(C)(C)c1nc(N2CC[C@H](OC(=O)C(F)(F)F)C2)c2nn[nH]c2n1]
in the presence of base, to afford (S)-1-[5-tert-butyl-3-(1-methyl-1H-tetrazol-5-ylmethyl)-3H-[1,2,3]triazolo[4,5-d]pyrimidin-7-yl]-pyrrolidin-3-ol
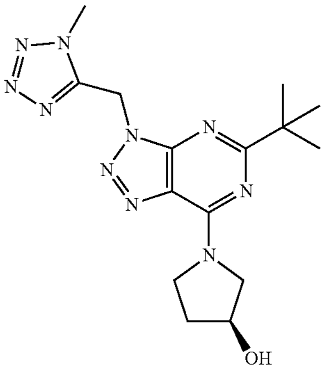
.
* * * * *